(12) United States Patent
Yuzhakov

(10) Patent No.: US 8,414,548 B2
(45) Date of Patent: Apr. 9, 2013

(54) METHOD OF MAKING MICRONEEDLE ARRAY AND DEVICE FOR APPLYING MICRONEEDLE ARRAY TO SKIN

(76) Inventor: Vadim V. Yuzhakov, Alameda, CA (US)

( * ) Notice: Subject to any disclaimer, the term of this patent is extended or adjusted under 35 U.S.C. 154(b) by 619 days.

(21) Appl. No.: 12/694,314

(22) Filed: Jan. 27, 2010

(65) Prior Publication Data
US 2010/0130940 A1 May 27, 2010

Related U.S. Application Data

(62) Division of application No. 11/328,813, filed on Jan. 10, 2006, now Pat. No. 7,658,728.

(51) Int. Cl.
*A61M 5/32* (2006.01)
*B22D 17/00* (2006.01)

(52) U.S. Cl. .................................................. 604/272

(58) Field of Classification Search ............. 604/20–22, 604/46, 164.01, 164.09, 172, 272–274, 890.1; 164/47, 113
See application file for complete search history.

(56) References Cited

U.S. PATENT DOCUMENTS

| | | | |
|---|---|---|---|
| 2,893,392 A | 7/1959 | Wagner et al. | |
| 3,072,122 A | 1/1963 | Rosenthal | |
| 3,814,097 A | 6/1974 | Ganderton et al. | |
| 3,964,482 A | 6/1976 | Gerstel et al. | |
| 4,983,377 A | 1/1991 | Murphy et al. | |
| 4,983,418 A | 1/1991 | Murphy et al. | |
| 5,156,591 A | 10/1992 | Gross et al. | |
| 5,250,023 A | 10/1993 | Lee et al. | |
| 5,279,543 A | 1/1994 | Glikfeld et al. | |
| 5,279,544 A | 1/1994 | Gross et al. | |
| 5,362,307 A | 11/1994 | Guy et al. | |
| 5,547,467 A | 8/1996 | Pliquett et al. | |
| 5,667,491 A | 9/1997 | Pliquett et al. | |
| 5,911,223 A | 6/1999 | Weaver et al. | |
| 6,083,196 A | 7/2000 | Trautman et al. | |
| 6,256,533 B1 | 7/2001 | Yuzhakov et al. | |
| 6,312,612 B1 | 11/2001 | Sherman et al. | |
| 6,334,856 B1 | 1/2002 | Allen et al. | |
| 6,379,324 B1 | 4/2002 | Gartstein et al. | |
| 6,451,240 B1 | 9/2002 | Sherman et al. | |
| 6,471,903 B2 | 10/2002 | Sherman et al. | |
| 6,503,231 B1 | 1/2003 | Prausnitz et al. | |
| 6,537,264 B1 * | 3/2003 | Cormier et al. ............... 604/506 |
| 6,565,532 B1 | 5/2003 | Yuzhakov et al. | |
| 6,611,707 B1 | 8/2003 | Prausnitz et al. | |
| 6,652,478 B1 | 11/2003 | Gartstein et al. | |

(Continued)

*Primary Examiner* — Kevin C Sirmons
*Assistant Examiner* — Andrew Gilbert
(74) *Attorney, Agent, or Firm* — Sutherland Asbill & Brennan LLP

(57) ABSTRACT

Microneedle arrays and drug delivery devices are provided for transdermally delivering a drug formulation to a patient. The microneedle array device includes a substantially planar substrate having an array of apertures; and a plurality of microneedles projecting at angle from the planar substrate, the microneedles having a base portion integrally connected to the substrate, a tip end portion distal to the base portion, and body portion therebetween, wherein each microneedle has at least one channel extending substantially from the base portion through at least a part of the body portion, the channel being open along at least part of the body portion and in fluid communication with at least one of the apertures in the substrate. In a preferred embodiment, each microneedle has a substantially rectangular cross-sectional shape and the channel is open to two opposing surfaces of the microneedle.

9 Claims, 6 Drawing Sheets

U.S. PATENT DOCUMENTS

| | | |
|---|---|---|
| 6,743,211 B1 | 6/2004 | Prausnitz et al. |
| 6,931,277 B1 | 8/2005 | Yuzhakov et al. |
| 7,658,728 B2 * | 2/2010 | Yuzhakov .................... 604/272 |
| 2002/0020688 A1 | 2/2002 | Sherman et al. |
| 2002/0082527 A1 | 6/2002 | Lie et al. |
| 2002/0082543 A1 | 6/2002 | Park et al. |
| 2002/0138049 A1 | 9/2002 | Allen et al. |
| 2002/0168290 A1 | 11/2002 | Yuzhakov et al. |
| 2002/0177858 A1 | 11/2002 | Sherman et al. |
| 2003/0028087 A1 | 2/2003 | Yuzhakov et al. |
| 2003/0028125 A1 | 2/2003 | Yuzhakov et al. |
| 2003/0143113 A2 | 7/2003 | Yuzhakov et al. |
| 2003/0150745 A1 | 8/2003 | Teodorczky et al. |
| 2003/0199810 A1 * | 10/2003 | Trautman et al. ............... 604/46 |
| 2003/0208167 A1 | 11/2003 | Prausnitz et al. |
| 2003/0211619 A1 | 11/2003 | Olson et al. |
| 2003/0212344 A1 | 11/2003 | Yuzhakov et al. |
| 2003/0212345 A1 | 11/2003 | McAllister et al. |
| 2003/0212346 A1 | 11/2003 | Yuzhakov et al. |
| 2003/0223906 A1 | 12/2003 | McAllister et al. |
| 2004/0106904 A1 | 6/2004 | Gonnelli et al. |
| 2005/0049549 A1 * | 3/2005 | Wong et al. ..................... 604/46 |
| 2005/0137525 A1 | 6/2005 | Wang et al. |
| 2005/0137531 A1 | 6/2005 | Prausnitz et al. |
| 2005/0187525 A1 | 8/2005 | Hilgers et al. |
| 2005/0209565 A1 | 9/2005 | Yuzhakov et al. |
| 2005/0261631 A1 | 11/2005 | Clarke et al. |
| 2007/0161964 A1 | 7/2007 | Yuzhakov et al. |

* cited by examiner

METHOD OF MAKING MICRONEEDLE ARRAY AND DEVICE FOR APPLYING MICRONEEDLE ARRAY TO SKIN

CROSS-REFERENCE TO RELATED APPLICATIONS

This is a divisional of U.S. application Ser. No. 11/328,813, filed Jan. 10, 2006, now U.S. Pat. No. 7,658,728, which is incorporated herein by reference in its entirety.

BACKGROUND OF THE INVENTION

This invention is generally in the field of devices for the administration of drugs to patients through the skin. More particularly, this invention relates to microneedle arrays and methods for transdermal drug delivery.

Transdermal drug delivery provides several advantages over other routes for administering a drug formulation to a patient. For example, oral administration of some drugs may be ineffective because the drug is destroyed in the gastrointestinal tract or eliminated by the liver, both of which are avoided by transdermal drug delivery. Parenteral injection with a conventional hypodermic needle also has drawbacks, as it is often painful and inconvenient. Although transdermal drug delivery avoids these problems, there are obstacles to its use. In particular, the transport of drug molecules through the intact stratum corneum, the outer layer of the skin, is often quite difficult due to the barrier properties of the stratum corneum. These barrier properties only allow relatively small molecules to be transported through the intact stratum corneum, and many useful drugs are too large to pass through the stratum corneum without some type of modification of the stratum corneum or other transport enhancement. Various transdermal enhancement methods are known, including those based on iontophoresis, ultrasound, and chemical penetration enhancers. However, these methods may be inadequate to assist in the delivery of many medications through an intact skin layer and/or they may be inconvenient or undesirably complicated to use.

Several methods have been recently proposed for making small pores in the stratum corneum in order to overcome its barrier properties. For example, patents to Altea Therapeutics disclose the use of arrays of micro-heaters for creating tiny holes in the stratum corneum, as well as the use of miniature pyramidal projections to porate the stratum corneum. See, e.g., U.S. Pat. No. 6,142,939 to Eppstein et al. and U.S. Pat. No. 6,183,434 to Eppstein. Others, including Procter & Gamble, Alza Corporation, and scientists and engineers at the University of California, Berkeley and at the Georgia Institute of Technology, have been working on the development of microneedle arrays that would make a large number of tiny holes in the stratum corneum. See, e.g., U.S. Pat. No. 6,611,707 to Prausnitz et al. and U.S. Pat. No. 6,334,856 to Allen et al.

These known microneedle array generally fall into one of two design categories: (1) solid microneedles and (2) microneedles with a central hollow bore, which are similar to conventional hypodermic needle. Solid microneedle arrays are essentially arrays of projections that are used to make holes in the stratum corneum and are subsequently removed before a drug is applied to the skin. If solid microneedle arrays are kept in the skin, then the drug cannot readily flow into and through the holes in the skin because the holes remain plugged by the microneedles. In an apparent effort to work around this problem, Alza Corporation discloses a method of depositing a drug directly on the surface of these solid microneedles. However, the deposition process is unreliable, and the thin layer of drug formulation on the microneedle could be easily chipped off of the microneedle during storage, transport, or administration (insertion) of the microneedles. Moreover, application of a thicker and stronger layer of drug formulation was found to be undesirable because it reduced the sharpness of the microneedles and therefore made insertion more difficult and painful. In response to this deficiency with the thicker drug coating, Alza Corporation disclosed a special insertion device, because patients are unable to insert the microneedle array by their selves without it. It therefore would be desirable to provide a microneedle array for drug delivery that avoids the disadvantages associated with known solid microneedle array designs.

Conventional hollow microneedles with a central bore are expensive to make and require exotic and expensive microfabrication methods. In particular, it is difficult to make sharp tips on hollow microneedles. Consequently, insertion of the microneedles into a patient's skin can be difficult and often painful. In addition, the central bore of the microneedle is quite small and may be easily plugged by skin tissue during the insertion process, thereby blocking the drug delivery conduit. Furthermore, because the length of microneedle central bore is much greater than its diameter, the diffusional transport of the drug through the central bore may be unacceptably slow. It may be even slower than the diffusion of the drug through the stratum corneum in the absence of the microneedle. It therefore would be desirable to provide a microneedle array for drug delivery that avoids the disadvantages associated with known hollow microneedle array designs.

U.S. Patent Application Publication No. 2003/0028125 discloses devices and methods for piercing the skin and accessing and collecting a physiological fluid sample therein. The disclosed device is unsuitable for drug delivery to the stratum corneum, in particular because the needle design is too large for such applications.

In summary, there is a need for a simple, effective, and economically desirable device for transdermal administration of a variety of drug types to a patient.

SUMMARY OF THE INVENTION

Microneedle arrays and drug delivery devices incorporating the microneedle arrays are provided, along with methods of making microneedle arrays and using microneedle arrays and devices to deliver a drug formulation through a biological barrier, such as the stratum corneum of human skin.

In one aspect, a microneedle array device is provide which includes a substantially planar substrate having an array of spaced apertures therein; and a plurality of microneedles projecting at angle from the plane in which the planar substrate lies, the microneedles having a base portion integrally connected to the substrate, a tip end portion distal to the base portion, and body portion therebetween, wherein at least one of the microneedles has at least one channel extending substantially from the base portion through at least a part of the body portion, the channel being open along at least part of the body portion and in fluid communication with at least one of the apertures in the substrate. In a preferred embodiment, the at least one of the microneedles has a substantially rectangular cross-sectional shape in a plane parallel to the substrate. In one specific variation of this embodiment, the at least one channel is open to two opposing surfaces of the microneedle.

In another embodiment, the tip end portion of the at least one of the microneedles is tapered. In a specific embodiment, the at least one channel terminates in the body portion of the microneedle and does not extend into the tapered tip portion.

In a preferred embodiment, the substrate and the microneedles comprise at least one biocompatible metal, such as a stainless steel. In another embodiment, the substrate and the microneedles comprise at least one biocompatible polymer.

In one embodiment, the length of the at least one microneedle may be between 10 µm and 1000 µm, preferably between 100 µm and 500 µm. In another embodiment, the at least one microneedle has a maximum width dimension of 500 µm.

In one embodiment, the body portion of the at least one microneedle is rectangular with a centrally located channel extending through the opposed longer sides of the body portion. In one particular embodiment, the rectangular body portion has a long side cross-sectional dimension between 1 and 500 µm and a short side cross-sectional dimension between 1 and 200 µm.

In one embodiment, the apertures in the substrate are polygonal in shape, each aperture being defined by three or more interior side surfaces in the substrate. In one embodiment, the base portion of the at least one microneedle includes a curved portion that extends from at least one of the interior side surfaces of the substrate. In one embodiment, a proximal end of the at least one channel extends to or into the at least one of the interior side surfaces of the substrate.

In another aspect, a device for transdermal administration of a drug is provided, which includes a substantially planar substrate having an array of spaced apertures therein; a plurality of microneedles projecting at angle from the plane in which the planar substrate lies, the microneedles having a base portion integrally connected to the substrate, a tip end portion distal to the base portion, and body portion therebetween, wherein at least one of the microneedles has at least one channel extending substantially from the base portion through at least a part of the body portion, the channel being open along at least part of the body portion and in fluid communication with at least one of the apertures in the substrate; and at least one drug storage element, which contains a drug formulation, positioned adjacent to the planar substrate. In a preferred embodiment, the at least one of the microneedles has a substantially rectangular cross-sectional shape in a plane parallel to the substrate. The at least one channel may be open to two opposing surfaces of the microneedle.

In one embodiment, the drug storage element is attached to a first surface of the planar substrate, the first surface being opposed to a second surface of the planar substrate of the microneedle array, wherein the microneedles project from the second surface.

In another embodiment, the device further includes a release mechanism for releasing the drug formulation from the drug storage element to permit the drug formulation to be transported into and through the at least one channel of the at least one microneedle. The release mechanism may utilize a mechanical force, heat, a chemical reaction, an electric field, a magnetic field, a pressure field, ultrasonic energy, vacuum, pressure, or a combination thereof.

In one embodiment, the drug storage element includes a porous material, wherein the drug formulation is stored in pores of the porous material. In another embodiment, the drug storage element includes at least one sealed reservoir. In one variation of this embodiment, the device further includes at least one puncturing barb extending from the first surface of the planar substrate, wherein the puncturing barb can be used to puncture the sealed reservoir.

In a preferred embodiment, the device further includes a backing structure and adhesive surface suitable for securing the device to the skin of a patient during administration of the drug formulation to the patient.

In still another aspect, a method is provided for manufacturing a microneedle array. In one embodiment, the method includes the steps of forming a substantially planar substrate having an array of spaced apertures therein; and forming a plurality of microneedles projecting at angle from the plane in which the planar substrate lies, the microneedles having a base portion integrally connected to the substrate, a tip end portion distal to the base portion, and body portion therebetween, wherein at least one of the microneedles has at least one channel extending substantially from the base portion through at least a part of the body portion, the channel being open along at least part of the body portion and in fluid communication with at least one of the apertures in the substrate. In various embodiments, the step of forming the plurality of microneedles comprises embossing, injection molding, casting, photochemical etching, electrochemical machining, electrical discharge machining, precision stamping, high-speed computer numerically controlled milling, Swiss screw machining, soft lithography, directional chemically assisted ion etching, or a combination thereof.

In a preferred embodiment, a method for manufacturing a microneedle array is provided that includes the steps of providing a substantially planar substrate material; forming a plurality of first apertures in the substrate material, wherein the interior surface of at least one of the first apertures defines a microneedle having a tip, a base, and a body portion therebetween; forming a plurality of second apertures in the substrate material, which at least one of the second apertures defines a channel located in the body portion of the microneedle; and bending the microneedle near its base such that the tip projects out of the plane of the substrate material. In one embodiment, the step of forming the first apertures, the forming the second apertures, or the forming both the first and second apertures includes removing portions of the substrate material by a process comprises embossing, injection molding, casting, photochemical etching, electrochemical machining, electrical discharge machining, precision stamping, high-speed computer numerically controlled milling, Swiss screw machining, soft lithography, directional chemically assisted ion etching, or a combination thereof. In one embodiment, the bending of the microneedle comprises direct or indirect application of a compressive force, heat, or a combination thereof, to the microneedle and/or substrate.

In still another aspect, a method is provided for administering a drug to a patient in need thereof, which includes the steps of inserting into the skin of the patient the microneedles of the microneedle devices described above, and causing the drug formulation to be transported from the drug storage element through the at least one channel of the microneedle and through the stratum corneum of the skin. The transport of the drug formulation may be driven or assisted by capillary force, gravitational force, overpressure, vacuum, an electric field, a magnetic field, iontophoresis, a molecular concentration gradient, or a combination thereof.

In a further aspect, an applicator device is provided for applying a microneedle array to skin. In one embodiment, the applicator device includes a housing having a substantially planar application side and an opposed top side; a recess in the housing in which a drug delivery device that includes a microneedle array can be stored; and a button on the top side of the housing, which button can be depressed to drive the drug delivery device out of the recess with the microneedles oriented substantially perpendicular to the planar application side. In one embodiment, the housing further comprises a roller disposed partially in a cavity on the planar application side of the housing.

In a preferred embodiment, the applicator device further includes one or more of the drug delivery devices described above that includes a microneedle array, wherein the device comprises a substantially planar substrate having an array of spaced apertures therein; a plurality of microneedles projecting at angle from the plane in which the planar substrate lies, the microneedles having a base portion integrally connected to the substrate, a tip end portion distal to the base portion, and body portion therebetween, wherein at least one of the microneedles has at least one channel extending substantially from the base portion through at least a part of the body portion, the channel being open along at least part of the body portion and in fluid communication with at least one of the apertures in the substrate; and at least one drug storage element, which contains a drug formulation, positioned adjacent to the planar substrate.

BRIEF DESCRIPTION OF THE DRAWINGS

FIG. 5A shows the application side, and FIG. 5B shows the actuation side.

DETAILED DESCRIPTION OF THE PREFERRED EMBODIMENT

Figure 1:
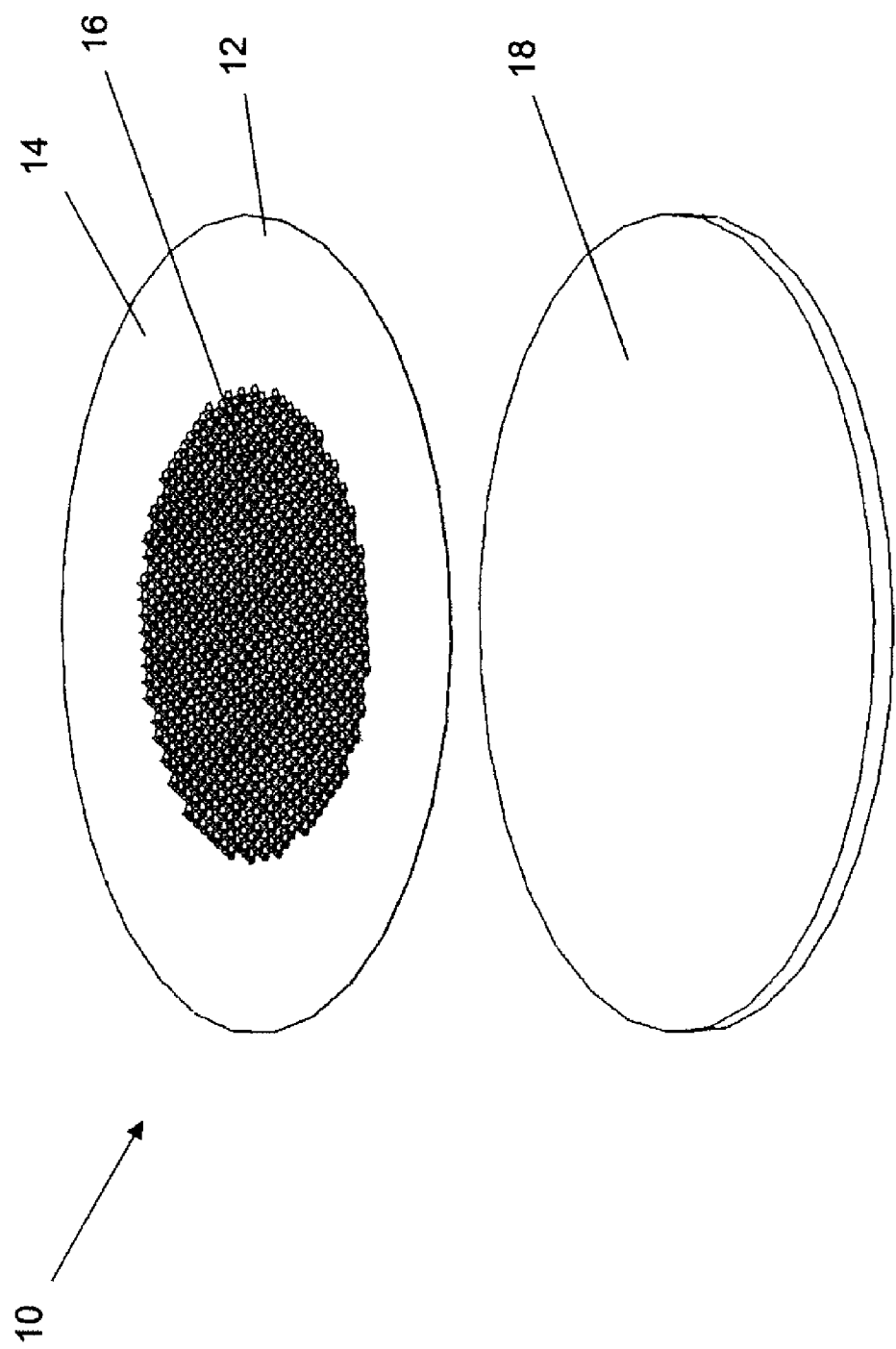
FIG. 1 is an exploded, perspective view of one embodiment of a transdermal drug delivery device comprising an array of microneedles and a drug storage element.

Improved microneedle arrays and transdermal drug delivery devices have been developed. The microneedles of the array combine the advantages of prior solid microneedles and prior microneedles with a central hollow bore, and avoid disadvantages of each. In particular, the present microneedles advantageously have both a strong, small solid tip and a channel for drug to flow through the stratum corneum and into the patient's lower skin tissues (e.g., epidermis, dermis, or subcutaneous skin layers) while the microneedle remains inserted in the patient's skin during drug delivery. Consequently, drug delivery rates can be maintained relatively constant because the created pores are kept open by the microneedles inserted into the patient's stratum corneum, and pain from insertion of the microneedles can be minimized since the tip portion of the microneedle can be made to have a smaller cross-section and sharper tip than conventional drug-coated solid microneedles or hollow microneedles with a central bore. In addition, mass transport using the present microneedles can be increased relative to similarly dimensioned hollow or solid conventional microneedles. A still further advantage of the present array design is that it may be fabricated using relatively easy and relatively inexpensive techniques, compared to those techniques required to make conventional hollow microneedles having a central bore.

Applicator devices have also been developed for applying the microneedle drug delivery devices (e.g., patches) to a patient's skin.

As used herein, the terms "comprise," "comprising," "include," and "including" are intended to be open, non-limiting terms, unless the contrary is expressly indicated.

Microneedle Array

The microneedle array comprises at least one substrate and a plurality of microneedles projecting at an angle from the at least one substrate. In one embodiment, a microneedle array device is provided which includes a substantially planar substrate having an array of spaced apertures therein. A plurality of microneedles project at angle from the plane in which the planar substrate lies. The microneedles have a base portion connected to the substrate, a tip end portion distal to the base portion, and body portion therebetween. At least one of the microneedles has at least one channel extending substantially from the base portion through at least a part of the body portion, the channel being open along at least part of the body portion and in fluid communication with at least one of the apertures in the substrate.

Generally, the microneedle can be in any elongated shape suitable for providing the skin piercing and fluid conduit functions, with minimal pain to the patient. In various embodiments, the microneedle is substantially cylindrical, wedge-shaped, cone-shaped, or triangular (e.g., blade-like). The cross-sectional shape (cut along a plane approximately parallel to the planar substrate or approximately perpendicular to the longitudinal axis of the microneedle) of the microneedle, or at least the portion of microneedle that is penetrable into the skin, may take a variety of forms, including rectangular, square, oval, circular, diamond, triangular, or star-shaped. In a preferred embodiment, the microneedle has a substantially rectangular cross-sectional shape in a plane parallel to the substrate. In one specific variation of this embodiment, the channel is open to two opposing surfaces of the microneedle.

The tip portion of the microneedle is designed to pierce a biological barrier, e.g., to pierce the stratum corneum of the skin of a patient, to form a conduit through which a drug formulation can be transported into the patient's tissue. To provide minimal pain to the patient, the tip portion of the microneedle should be sufficiently small and sharp to enable piercing and penetration of the skin with minimal pain. In a preferred embodiment, the tip end portion of the microneedle is tapered from the body portion toward the tip end, defining a point or apex at the end of the microneedle. In one preferred variation, the channel terminates in the body portion of the microneedle and does not extend into the tapered tip portion, such that microneedle tapers toward the tip at a point beyond the end of the channel. In various embodiments, the tapered tip portion may be in the form of an oblique angle at the tip, or a pyramidal or triangular shape.

The dimensions of the microneedles may vary depending on a variety of factors such as the type of drug to be delivered, the dosage of the drug to be delivered, and the desired penetration depth. Generally, the microneedles are constructed to provide skin-piercing and fluid delivery functions and thus will be designed to be sufficiently robust to withstand insertion into and withdrawal from the skin. Each microneedle has a length of about 1 micrometer ($\mu m$) to about 5000 micrometers ($\mu m$). More preferably, each microneedle has a length of about 1 $\mu m$ to about 500 $\mu m$. Still more preferably, each microneedle has a length of about 100 $\mu m$ to about 500 $\mu m$. The penetration length of the microneedles into the biological barrier is about 50 $\mu m$ to about 200 $\mu m$. In addition, each of the microneedles has a width of about 1 $\mu m$ to about 500 $\mu m$.

Furthermore, each microneedle has a thickness of about 1 μm to about 200 μm. It will be understood by one skilled in the art that the width and thickness of the microneedle may vary along its length. For instance, the base portion may be wider (thicker) than the body portion, or the body portion may have a slight taper approaching the tip portion.

The one or more channels in each microneedle provide a path for a drug formulation to flow from the apertures in the substrate through/into the biological barrier at the site of piercing. The channel preferably extends from the substrate toward the tip through a substantial portion of a length dimension of the microneedles. The channel does not extend all the way to the tip of the microneedle as a central bore would. The channel may comprise an opening through two surfaces of the microneedle. In alternate embodiments, the channel may comprise any shape suitable to deliver fluid proximal to the microneedle tip. For example, the channel may comprise a groove on one surface of the microneedle that is only open to the outside environment on one side of the microneedle. In addition, the channel may be dimensioned to provide a capillary force or effect upon the fluid to be delivered such that the capillary effect draws or wicks fluid into the base portion of the microneedle from the substrate aperture, through the body portion of the microneedle, and toward the tip portion of the microneedle. In other embodiments, each microneedle may have more than one channel, for example, two narrower channels in parallel.

The width of the channel may be constant along its length or may vary. The length of the channel will vary depending on a variety of factors, but will typically be about 50 to 99% of the length of the microneedle, and preferably is about 70 to 99% of the length of the microneedle. Nevertheless, it is possible that in certain embodiments the length of the channel will be between 1 to 50% of the length of the microneedle. As such, the length of the tip portion beyond the channel may vary, but usually is about 1 to 50% of the length of the microneedle, and more usually is about 1 to 30% of the length of the microneedle. It will be appreciated by one skilled in the art that the width of the channel, the length of the channel, and the length of the microneedle may be varied to increase or decrease the flow rate of the drug.

In one embodiment, the length of the at least one microneedle may be between 10 μm and 1000 μm, preferably between 100 μm and 500 μm. In another embodiment, the at least one microneedle has a maximum width dimension of 500 μm. In one embodiment, the body portion of the microneedle is rectangular with a centrally located channel extending through the opposed longer sides of the body portion. In one particular embodiment, the rectangular body portion has a long side cross-sectional dimension between 1 μm and 500 μm and a short side cross-sectional dimension between 1 μm and 200 μm.

The apertures in the planar substrate may be in essentially any shape. In various embodiments, the apertures may be circular, semi-circular, oval, diamond, triangular, or a combination thereof. In a preferred embodiment, the apertures in the substrate are polygonal in shape, each aperture being defined by three or more interior side surfaces in the substrate. In one embodiment, the base portion of the at least one microneedle includes a curved portion that extends from at least one of the interior side surfaces of the substrate. In one embodiment, a proximal end of the at least one channel extends to or into the at least one of the interior side surfaces of the substrate.

In preferred embodiments, the substrate, the microneedles, or both, are formed of, or coated with, a biocompatible material. The microneedles may be formed from the substrate material, or alternatively, the microneedles can include a material different from the substrate material. Representative examples of suitable materials of construction include metals and alloys such as stainless steels, palladium, titanium, and aluminum; plastics such as polyetherimide, polycarbonate, polyetheretherketone, polyimide, polymethylpentene, polyvinylidene fluoride, polyphenylsulfone, liquid crystalline polymer, polyethylene terephthalate (PET), polyethylene terephthalate-glycol modified (PETG), polyimide, and polycarbonate; and ceramics such as silicon and glass. The material preferably is selected such that the microneedle is strong enough at its designed dimensions for the microneedle to effectively pierce the biological barrier(s) of choice, without significant bending or breaking of the microneedle. The microneedle and substrate materials also should be non-reactive with the drug formulation being delivered through substrate apertures and microneedle channel(s). In a preferred embodiment, the microneedles and substrate consist of a metal or alloy. In another embodiment, the microneedles comprise a biocompatible thermoplastic polymer.

The substrate, the microneedles, or both, optionally may further include secondary materials of construction embedded therein or coated thereon. For example, microparticles, nanoparticles, fibers, fibrids, or other particulate materials may be included. Examples of such materials include metals, carbon siliceous materials, glasses, and ceramics. These secondary materials may enhance one or more physical or chemical characteristics of the microneedle array. For example, the secondary material may be insulating layer or may improve the flow or transport of the drug formulation through the apertures and channels of the array. Representative examples of suitable insulating materials include polyethylene terephthalate (PET), polyethylene terephthalate-glycol modified (PETG), polyimide, polycarbonate, polystyrene, silicon, silicon dioxide, ceramic, glass, and the like. In a preferred embodiment, chemical vapor deposited silicon dioxide is used as an insulating layer on the microneedle array due to its hydrophilic nature, which may facilitate fluid delivery. In another embodiment, the channel of the microneedle may include one or more agents to facilitate fluid flow. For example, one or more hydrophilic agents may be present on the interior surfaces defining the channel. Examples of such hydrophilic agents include, but are not limited to, surfactants. Exemplary surfactants include MESA, Triton, Macol, Tetronic, Silwet, Zonyl, and Pluronic.

The surface of the substrate that is in contact with the surface of the biological barrier (e.g., the stratum corneum) may be coated, in whole or in part, with a bonding substance that can secure the microneedle patch to the biological barrier for an extended period of time, e.g., for a duration required to release all of the drug formulation to the biological barrier. Examples of such bonding agents include adhesives and bioactive films, which are activated by pressure, heat, light (UV, visible, or laser), electric, magnetic fields, biochemical and electrochemical reactions, or a combination thereof.

Figure 2:
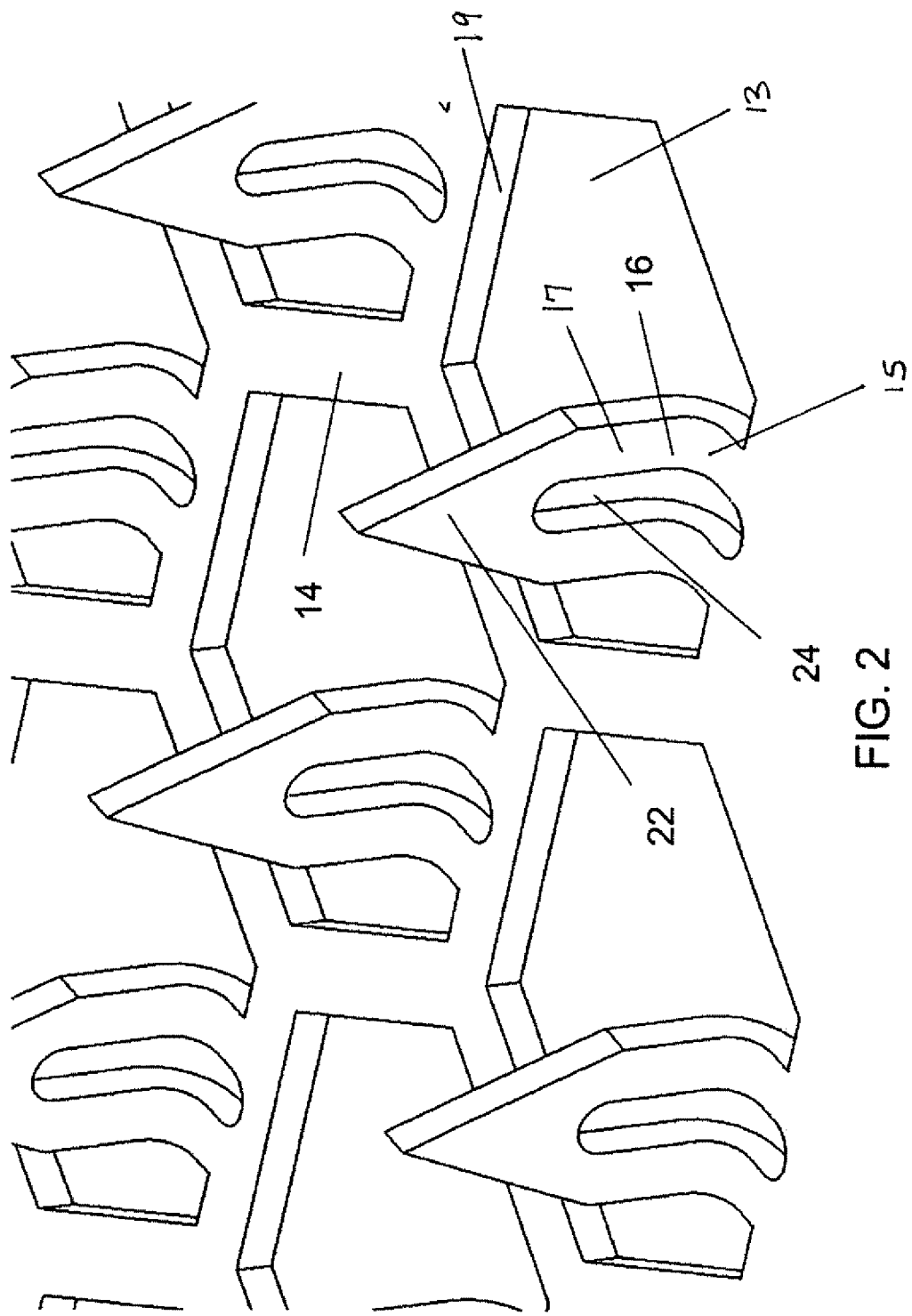
FIG. 2 is a close-up view of part of one embodiment of a microneedle array.

A representative embodiment of the microneedle array is shown in FIG. 1 and FIG. 2. The microneedle array 12 includes a substantially planar substrate 14 and a plurality of microneedles 16 extending from the planar substrate 14. The planar substrate 14 includes a plurality of spaced apertures 13. The planar substrate 14 optionally may be coated with a bonding substance (not shown) to facilitate adhesion of the microneedle array 12 to a surface of a biological barrier. Each of the microneedles 16 has a base portion 15 connected to the planar substrate, a tip end portion 22 distal to the base portion 15, and a body portion 17 therebetween. Each microneedle has an elongated channel 24 extending from the base portion 15 through at least a part of the body portion 17. The channel 24 is open along the body portion, through two opposing surfaces of the body portion, and the channel 24 is in fluid communication with aperture 13 in the planar substrate. The microneedles 16, or at least the body and tip portions thereof, are substantially perpendicular to the planar substrate 14. The apertures 13 in the substrate are hexagonal and defined by interior side surfaces 19 in the planar substrate. The base portion 15 of each of the microneedles includes a curved portion that is integrally connected to the planar substrate, extending from one of the interior side surfaces 19.

Microneedle Drug Delivery Device

In preferred embodiments, the microneedle array described in the preceding section is part of a drug delivery device that includes a drug storage element. The drug storage element is a means for containing a drug formulation for release to and through the microneedle array, for transdermal administration of the formulation via the microneedle array. Preferably, the drug delivery device is in the form of a transdermal drug delivery patch.

In a preferred embodiment, the drug storage element is positioned adjacent to the planar substrate. For example, the drug storage element may be attached to a first surface of the planar substrate, wherein the first surface is opposed to a second surface of the planar substrate from which the microneedles project. In a preferred embodiment, the drug delivery device is in the form of a patch that can be adhered to the skin during transdermal administration of a drug formulation through the microneedle array. In one embodiment, the device, or patch, includes a backing structure and adhesive surface suitable for securing the device to the skin of a patient with the microneedles in an inserted position in the skin.

In a preferred embodiment, the drug storage element has at least one sealed reservoir, which can be selectively punctured or otherwise breached in a controlled manner to release a drug formulation contained therein. In one embodiment, the drug storage element includes a porous material, wherein the drug formulation is stored in pores of the porous material. Representative examples of suitable porous materials include open cell polymeric foams, sheets/mats of woven or non-woven fibers, combinations thereof, and the like. In another example, the drug storage element may be in the form of one or more substantially flat pouches, for example, made of two sheets of flexible thermoplastic polymeric film, sealed along the edges to define a reservoir therebetween.

The "drug formulation" refers to essentially any therapeutic or prophylactic agent known in the art (e.g., an active pharmaceutical ingredient, or API), and typically includes one or more physiological acceptable carriers or excipients to facilitate transdermal administration of the drug formulation. In one embodiment, the drug formulation is a fluid drug formulation, wherein the formulation can flow through apertures and channels in the microneedle array; it may be a solution, suspension, emulsion, or a combination thereof. In another embodiment, the drug formulation comprises a solid formulation, wherein the transport of drug through apertures and channels in the microneedle array involves diffusional transport mechanisms, with little or no bulk flow. The drug delivery device may include a drug formulation that includes a combination of liquid and solid components, wherein transport of the drug formulation involves both flow and mass diffusion.

The drug delivery device typically includes means for causing the drug formulation to be released from the drug storage element, permitting the drug formulation to flow into or otherwise be transported through the channel of the microneedle. The release typically is to and through the apertures in the planar substrate and thus to the base end of the channel in the microneedle. A wide variety of release mechanisms for releasing the drug formulation from the drug storage element can be envisioned by those skilled in the art. These release mechanisms may utilize a mechanical force, heat, a chemical reaction, an electric field, a magnetic field, a pressure field, ultrasonic energy, vacuum, pressure, or a combination thereof. In one embodiment, the release mechanism includes a means for applying a compressive force to a porous material to expel the drug formulation from the pores in the porous material. The means for applying a compressive force can be in the form of a spring-biased piston or button that can be manually depressed to apply a direct or leveraged force onto the back of the drug storage element. The same force optionally may cause the microneedles to be inserted into the skin of a patient and/or cause a pressure-sensitive adhesive surface on the device (e.g., on the periphery of a backing material) to become adhered to the surface of the skin. In another embodiment, the drug delivery device includes at least one puncturing barb extending from the surface of the planar substrate (opposite the microneedle), wherein the puncturing barb can be used to puncture the sealed reservoir, e.g., upon application of a compressive force to the reservoir. This barb could be one or more microneedles bent in the opposite direction from the microneedles intended for skin insertion.

The flow of the drug formulation through the channels into the biological barrier may be passive, e.g., the result of capillary and gravitational forces. Alternatively, the flow may be actively assisted. In one embodiment, the drug delivery device may include means for actively driving the drug formulation through the microneedle channels and/or into the skin. For example, the flow of the drug formulation through the channels into the biological barrier may be aided by application of heat (e.g., generated by a series of microfabricated resistors), an electric field, a magnetic field, a pressure field, a concentration gradient, or any other physical force or energy. The application of an electric field can comprise electrophoresis, iontophoresis, electroosmosis, electroporation, or the like. The application of a magnetic field can comprise magnetophoresis or the like. The application of a pressure field can comprise pumping, applying ultrasonic energy, applying vacuum, pressure, or the like.

FIG. 1 shows a transdermal drug delivery patch 10 comprising a microneedle array 12 and a drug storage element 18, which is configured to store a drug formulation therein for subsequent release to the microneedle array.

Making the Microneedle Arrays

The microneedle arrays described herein can be made using or adapting a variety of fabrication techniques known in the art, depending upon the particular materials of construction and the particular microneedle/array design selected. In one embodiment, the microneedle array is made using one or more conventional microfabrication techniques. The microneedles may be formed individually or the whole array of microneedles and substrate may be formed in a single process. In a preferred embodiment, the microneedle arrays are formed in mass (i.e., commercial scale) quantities using inexpensive fabrication processes available in the art.

In one embodiment, the method for manufacturing a microneedle array includes the steps of forming a substantially planar substrate having an array of spaced apertures therein; and forming a plurality of microneedles projecting at angle from the plane in which the planar substrate lies, the microneedles having a base portion integrally connected to the substrate, a tip end portion distal to the base portion, and body portion therebetween, wherein at least one of the microneedles has at least one channel extending substantially from the base portion through at least a part of the body portion, the channel being open along at least part of the body portion and in fluid communication with at least one of the apertures in the substrate. In various embodiments, the step of forming the plurality of microneedles includes embossing, injection molding, casting, photochemical etching, electrochemical machining, electrical discharge machining, precision stamping, high-speed computer numerically controlled milling, Swiss screw machining, soft lithography, directional chemically assisted ion etching, or a combination thereof.

In one particular embodiment, the method for manufacturing a microneedle array includes the steps of providing a substantially planar substrate material; forming a plurality of first apertures in the substrate material, wherein the interior surface of at least one of the first apertures defines a microneedle having a tip, a base, and a body portion therebetween; forming a plurality of second apertures in the substrate material, which at least one of the second apertures defines a channel located in the body portion of the microneedle; and bending the microneedle near its base such that the tip projects out of the plane of the substrate material. In particular variations of this embodiment, the forming of the first apertures, the forming of the second apertures, or the forming of both the first and second apertures includes removing portions of the substrate material, proximate to each of the plurality of microneedles to shape each microneedle. This process may include embossing, injection molding, casting, photochemical etching, electrochemical machining, electrical discharge machining, precision stamping, high-speed computer numerically controlled milling, Swiss screw machining, soft lithography, directional chemically assisted ion etching, or a combination thereof. In one embodiment, the step of bending the microneedle comprises direct or indirect application of a compressive force, heat, or a combination thereof, to the microneedle and/or substrate.

The forming of the microneedles may include forming the microneedles in-plane with the substrate and then bending the plurality of microneedles out-of-plane with the substrate, for example, to a position substantially perpendicular to the planar substrate surface. Alternatively, the microneedles may be fabricated originally out-of-plane with the substrate (i.e., with no intermediate in-plane structure). For example, directional chemically assisted ion etching can be used to fabricate the microneedles that are initially out-of-plane with the substrate. These various microneedle fabrication options allow the microneedle arrays to be fabricated from flexible substrates and/or inflexible substrates.

In a preferred embodiment, microneedles may be formed in-plane or out-of-plane with the substrate using a microreplication technique known in the art. Representative examples of suitable microreplication techniques include embossing, injection molding and casting processes. Such microreplication techniques, and in particular embossing techniques, may provide low cost manufacturing and also may advantageously enable the tip of the microneedle to be extremely small (near infinitesimally small cross-sectional area) and sharp. Furthermore, embossing techniques allow precise, consistent fabrication of the microneedles.

In a preferred embodiment, an embossing technique is used. In one process using an embossing technique, a planar substrate material, such as a suitable thermoplastic precursor material, is placed into an embossing apparatus, where such an apparatus includes a mold having features of a microneedle array as described herein. (The mold may have a negative image of the features of the microneedles.) The precursor material is then compressed by the mold under heat and a suitable compression force. In one embodiment, the planar substrate material has a thickness in the range of about 25 μm to about 650 μm, preferably from about 50 μm to about 625 μm, and more preferably from about 75 μm to about 600 μm. In one embodiment, the substrate material is heated temperature in the range of about 20° C. to 1500° C., preferably from about 100° C. to 1000° C., more preferably from about 200° C. to 500° C. The heat is usually applied to the substrate material for about 0.1 seconds to 1000 seconds, preferably for about 0.1 seconds to 100 seconds, and more preferably about 0.1 seconds to 10 seconds. The compression force may range from about 1 GPa to 50 GPa, preferably from about 10 GPa to 40 GPa, and more preferably from about 20 GPa to 30 GPa. The compression force may be applied for about 0.01 seconds to 100 seconds, preferably for about 0.01 seconds to 10 seconds, and more preferably about 0.01 seconds to 1 second. The heat and compression force may be applied at the same time or different times. After the substrate material is cooled, it is removed from the embossing apparatus, yielding an embossed array of microneedles, which may be in-plane or out-of-plane. If the microneedles of the embossed array are in-plane with the substrate, then the microneedles subsequently are subjected to a bending step to fix them into an out-of-plane orientation relative to the substrate.

The step of bending in-plane microneedles of an intermediate structure into an out-of-plane position to form a microneedle array can be done using a variety of different methods, to effect application of a direct or indirect force that causes plastic and/or elastic deformation of the microneedles, preferably limited to the base portion thereof. In one example, the bending of the microneedles out-of-plane with the substrate may be facilitated by the use of a mold (e.g., a metal mold) having protrusions corresponding to the number and position of the microneedles in the intermediate structure, whereby the mold can be engaged (e.g., compressed) with the intermediate structure, the compressive force between the protrusions and the microneedles causing all of the microneedles to bend (at their base portions) simultaneously out-of-plane. In another example, the microneedle array can be pressed between a thick elastic film (e.g., rubber or polyurethane) and a mold having cavities corresponding to the number and position of the microneedles to bend the microneedles out-of-plane with the substrate simultaneously. The compressive force squeezes the thick elastic film into the cavities on the opposite side of the substrate, and the thick elastic film consequently bends the microneedles out-of-plane with the substrate and into the cavities.

Heat and/or various auxiliary pressures can be used in conjunction with the bending force to facilitate the bending of the microneedles. For example, a heated high-speed liquid or gas can be flowed in a direction substantially perpendicular to the plane of the substrate comprising plastic microneedles. The plastic microneedles are heated by the flowing fluid, undergo a plastic transition, and then are bent out-of plane with the substrate by the force of the high-speed fluid. In other embodiments, the step of bending the in-plane microneedles may include directly or indirectly applying an electric field or a magnetic field to microneedles.

Figure 3:
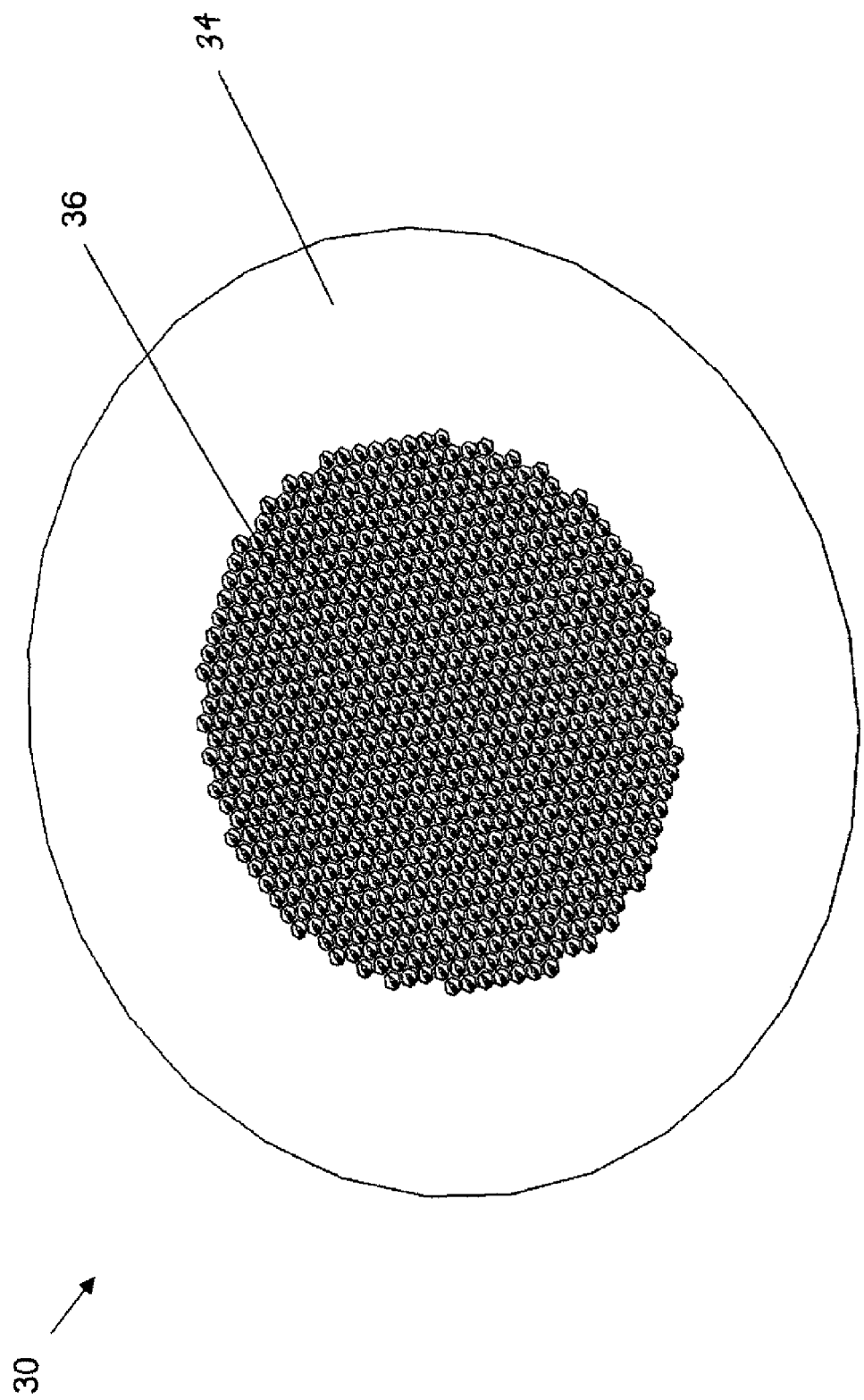
FIG. 3 is a plan view of one embodiment of an intermediate structure used in forming the microneedle array, wherein the microneedles of the intermediate structure are formed, and still are, in-plane with the substrate.
Figure 4:
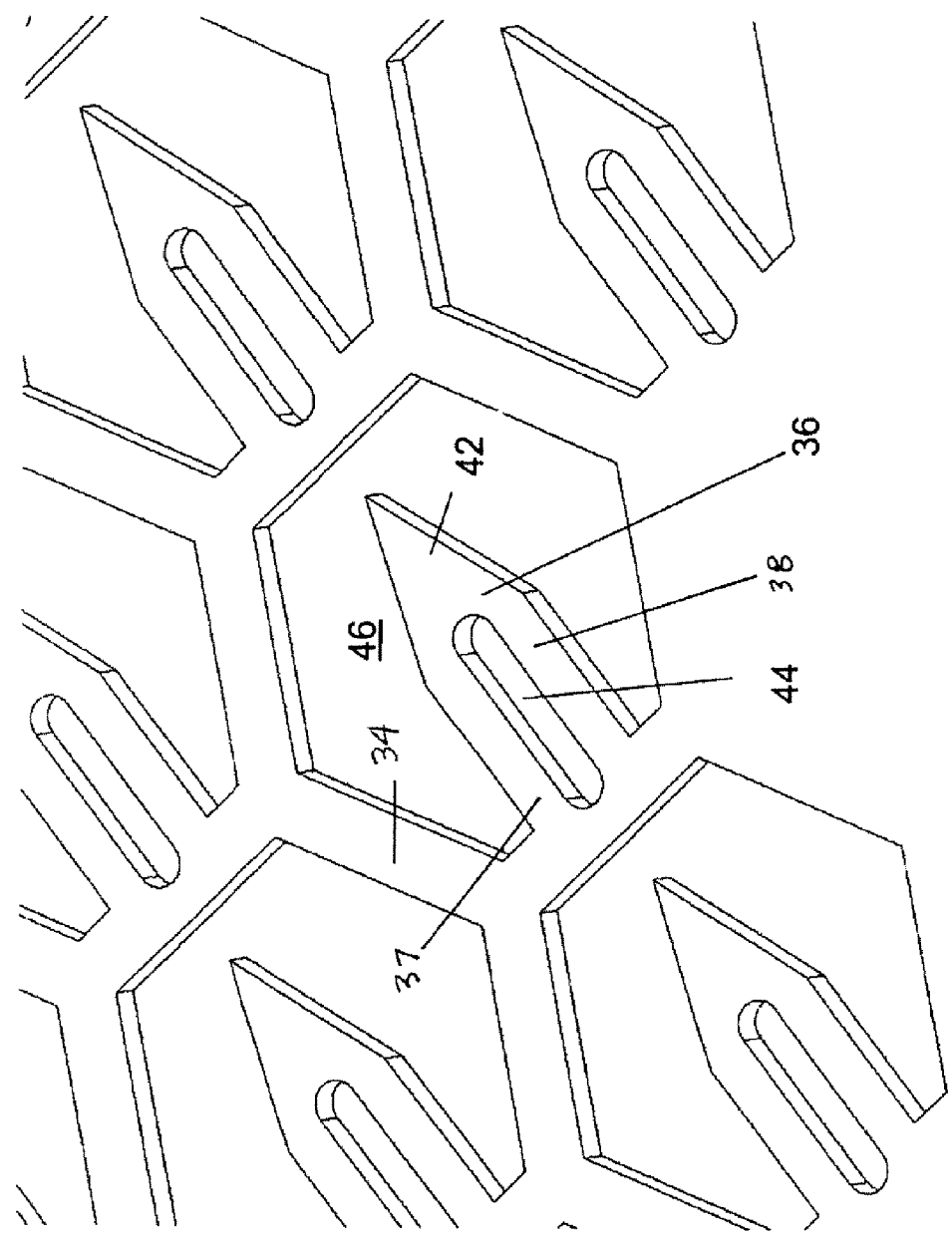
FIG. 4 is a close-up view of part of the intermediate microneedle structure shown in FIG. 3.

FIG. 3 and FIG. 4 illustrate one embodiment of an intermediate microneedle structure 30. Structure 30 includes a planar substrate 34 and a plurality of microneedles 36 positioned in apertures 46 in the planar substrate 34. The microneedles lie in the plane of the planar substrate. Each microneedle 36 has a base portion 37, a tip end portion 42, and a body portion 38 therebetween. Each microneedle 36 also has an elongated channel 44 in the base portion and body portion of each microneedle. To make a microneedle array for drug delivery from this intermediate structure, the microneedles 36 will be bent out-of-plane with the planar substrate 34.

The microneedle arrays and drug storage elements can be made separately and then assembled using known techniques for connecting conventional microneedle arrays to a drug storage element, which preferably is done in an aseptic or sterile environment.

Drug Device Applicator and Use of the Microneedle Array Devices

Drug delivery devices comprising the microneedle arrays described herein preferably are used to deliver a drug formulation across a biological barrier. The biological barrier preferably is human or other mammalian skin, although other tissue surfaces may be envisioned. In a typical use, the drug formulation is released from the drug storage element, it flows to the microneedle array, where it passes through the apertures in the planar substrate of the array and then enters the channels of the microneedles at the base portions of the microneedles. The drug formulation then is transported through the channel, traversing the stratum corneum and then entering the epidermis, dermis, and/or subcutaneous skin tissues. After administration of the drug formulation is complete, the microneedles are removed from the skin.

In a preferred embodiment, a method of administering a drug to a patient in need thereof includes the steps of inserting into the skin of the patient the microneedles of a drug delivery device that has a drug storage element containing a drug formulation, and then causing the drug formulation to be transported from the drug storage element, into and through at least one channel of at least one of the microneedle, and through the stratum corneum of the skin. The transport of the drug formulation can be passively or actively assisted. In various embodiments, the drug formulation is transported under the influence or assistance of capillary forces, gravitational forces, overpressure, vacuum, an electric field, a magnetic field, iontophoresis, a molecular concentration gradient, or a combination thereof. One skilled in the art can utilize or readily adapt any of these means using technology known in the art.

The microneedles of the drug delivery device can be inserted into the skin by a variety of means, including direct manual application or with the aid of an applicator device to insure uniform and proper microneedle penetration, consistently within a single array and across different arrays. The applicator device may be completely mechanical or it may be electromechanical. The applicator device may include pressure sensors in communication with an electronically controlled release mechanism, to insure that a drug delivery device is applied to the skin with the desired force each time. Optionally, the applicator device may include hardware, software, and power source components to provide heat, electrical field, magnetic field, pressure, or other drug delivery assistance means known in the art. The applicator device may include one or more rollers for use in applying an even pressure to the drug delivery patch to ensure that it is completely secured to the skin. The roller may, for example, further secure a pressure sensitive adhesive surface around the periphery of the patch.

Figure 5A:
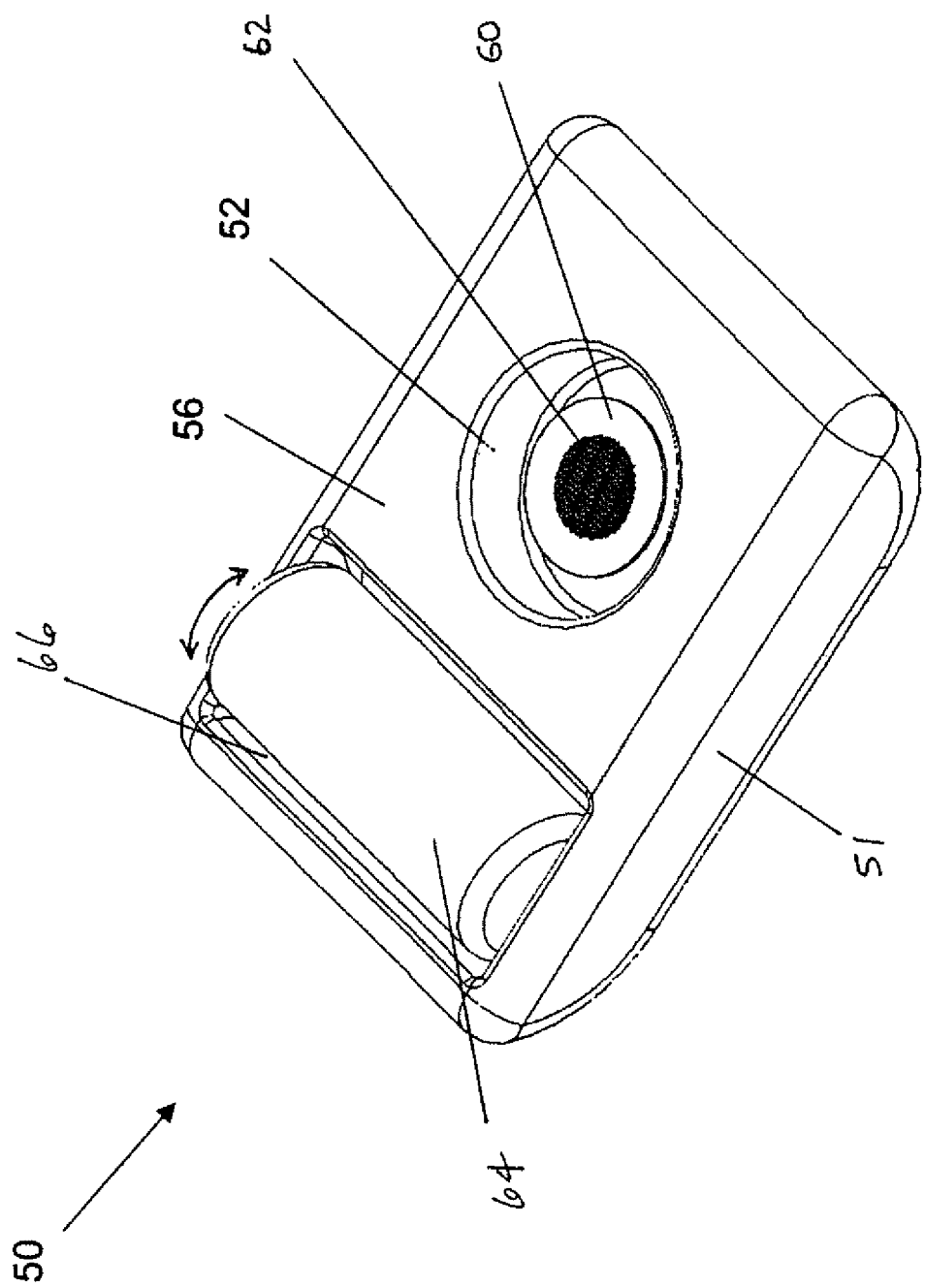
FIGS. 5A-B are perspective views of one embodiment of an applicator device for applying a microneedle drug delivery device to a patient's skin.
Figure 5B:
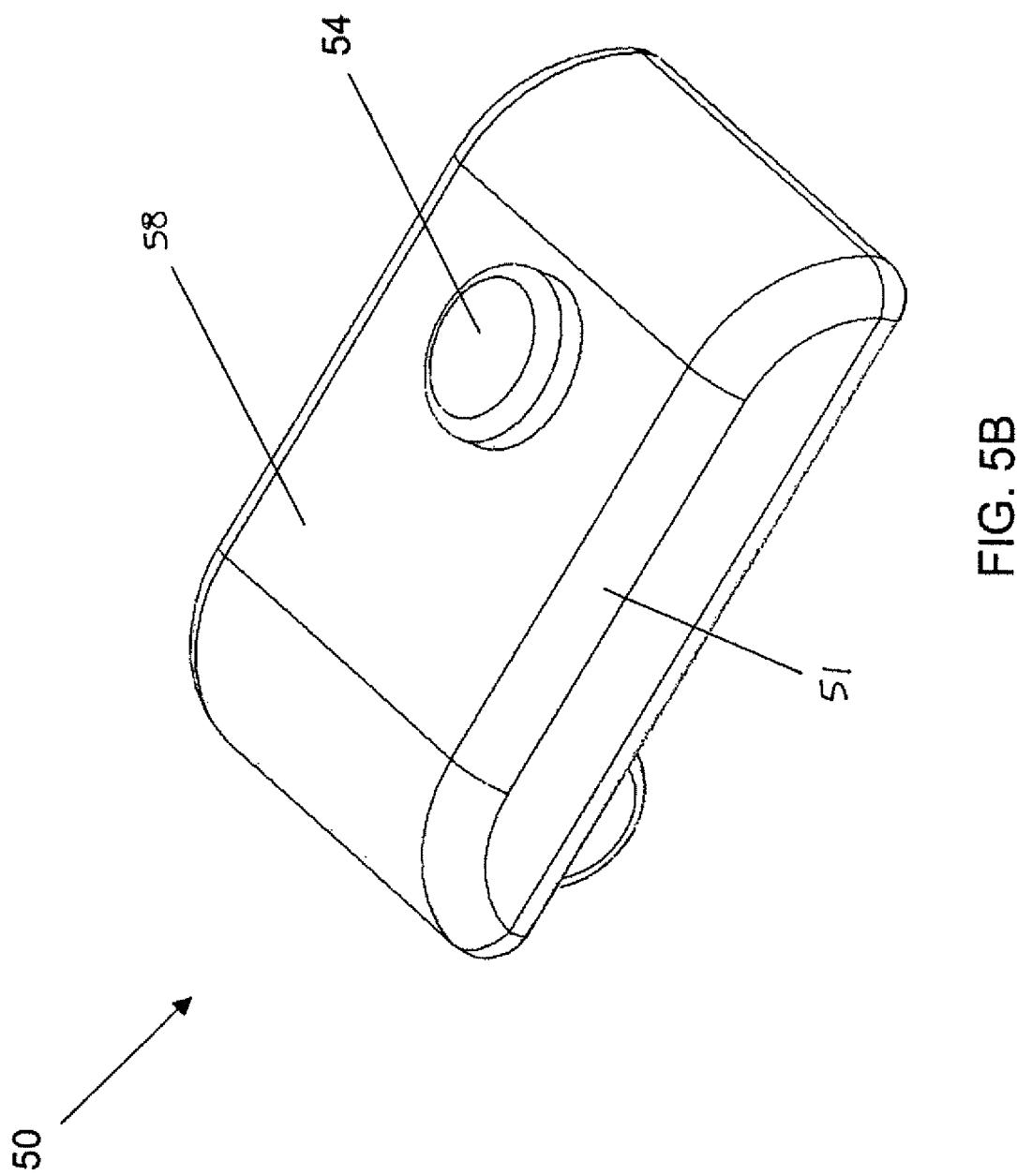

One example of a simple applicator device is shown in FIGS. 5A-B. Applicator device 50 includes a rigid housing 51 having a substantially planar application side 56 and an opposed actuation (top) side 58; a recess 52 in the housing in which a drug delivery device (i.e., a patch) 60 that includes a microneedle array 62 is disposed; and a button 54 on the top side of the housing 51. The button can be depressed to drive the drug delivery device 60 out of the recess 52 to and to drive the microneedles 62 into the skin (piercing the stratum corneum), when the application side is placed against the skin of a patient at the site for transdermal administration of the drug formulation. The housing further includes a roller 64 disposed partially in a cavity 66 on the application side of the housing. The roller 64 is used for completely inserting the microneedles 62 into the biological barrier as well as for establishing and facilitating a secure bond between the drug delivery device 60 and the surface of the biological barrier. The action of depressing the button 54 followed by application of the roller 64 also supplies a compressive force to the drug storage element (not shown) causing the drug formulation to be released from the drug storage element to the apertures and channels of the microneedle array. The roller 64 can also generate pressure, heat, light (e.g., UV, visible, or laser), electric, magnetic fields, biochemical and electrochemical reactions, or a combination thereof aimed to activate the bonding substance applied on the surface of the drug delivery device 60 which can hold the drug delivery device 60 attached to the biological barrier (not shown) for an extended period of time.

Publications cited herein are incorporated by reference. The foregoing description of various embodiments of the present invention is presented for purposes of illustration and description. The description is not intended to be exhaustive or to limit the invention to the precise form disclosed. The embodiments were chosen and described in order to best illustrate the principles of the invention and its practical application to thereby enable one of ordinary skill in the art to best utilize the invention and various embodiments with various modifications as are suited to the particular use contemplated. Modifications and variations of the methods and devices described herein will be obvious to those skilled in the art from the foregoing detailed description. Such modifications and variations are intended to come within the scope of the appended claims.

I claim:

1. A method for manufacturing a microneedle array comprising
providing a substantially planar substrate material;
forming a plurality of first apertures in the substrate material, wherein the interior surface of at least one of the first apertures defines a microneedle having a tip, a base, and a body portion therebetween;
forming a plurality of second apertures in the substrate material, each of the second apertures defining an elongated channel located in the body portion of the microneedle; and
bending the microneedle near its base such that the tip and body portion project out of the plane of the substrate material,
wherein the tip of the microneedle is tapered, the body portion is rectangular, and the channel extends through 50% to 99% of the length of the microneedle substantially from the planar substrate, through the base, and through at least a part of the body portion.

2. The method of claim 1, wherein the bending of the microneedle comprises direct or indirect application of a compressive force, heat, or a combination thereof, to the microneedle and/or substrate material.

3. The method of claim 1, wherein the substrate material and the microneedle comprise stainless steel or another biocompatible metal.

4. The method of claim 1, wherein the first apertures in the substrate material are polygonal in shape, each aperture being defined by three or more interior side surfaces in the substrate material.

5. The method of claim 1, wherein the microneedle has a length between 1 μm and 5000 μm.

6. The method of claim 1, wherein the microneedle has a length between 10 μm and 1000 μm.

7. The method of claim 1, wherein the microneedle has a width between 1 μm and 500 μm.

8. The method of claim 1, wherein the microneedle has a thickness between 1 μm and 200 μm.

9. The method of claim 1, wherein the steps of forming the first and second apertures comprise embossing, injection molding, casting, photochemical etching, electrochemical machining, electrical discharge machining, precision stamping, high-speed computer numerically controlled milling, Swiss screw machining, soft lithography, directional chemically assisted ion etching, or a combination thereof.

\* \* \* \* \*